United States Patent
Jiang et al.

(10) Patent No.: US 7,770,107 B2
(45) Date of Patent: Aug. 3, 2010

(54) METHODS AND SYSTEMS FOR EXTRACTING AND PROCESSING TRANSLATABLE AND TRANSFORMABLE DATA FROM XSL FILES

(75) Inventors: Xin Jiang, Foster City, CA (US); Shinji Yoshida, Belmont, CA (US); Itsuo Okamoto, Sunnyvale, CA (US)

(73) Assignee: Oracle International Corporation, Redwood Shores, CA (US)

( * ) Notice: Subject to any disclaimer, the term of this patent is extended or adjusted under 35 U.S.C. 154(b) by 1118 days.

(21) Appl. No.: 11/383,069

(22) Filed: May 12, 2006

(65) Prior Publication Data

US 2007/0208997 A1    Sep. 6, 2007

Related U.S. Application Data

(60) Provisional application No. 60/778,221, filed on Mar. 1, 2006.

(51) Int. Cl.
*G06F 17/00* (2006.01)
(52) U.S. Cl. ............... 715/236; 715/234; 715/235; 715/241
(58) Field of Classification Search .......... 715/236
See application file for complete search history.

(56) References Cited

U.S. PATENT DOCUMENTS

2001/0056504 A1* 12/2001 Kuznetsov ............ 709/310
2002/0035583 A1*  3/2002 Price et al. ............ 707/513
2002/0111963 A1*  8/2002 Gebert et al. ........... 707/513
2002/0147748 A1* 10/2002 Huang et al. ........... 707/517
2003/0037076 A1*  2/2003 Bravery et al. .......... 707/517
2003/0097635 A1*  5/2003 Giannetti ............ 715/501.1
2004/0261010 A1* 12/2004 Matsuishi ........... 715/501.1
2006/0242563 A1* 10/2006 Liu et al. ............. 715/513
2007/0150809 A1*  6/2007 Yoshida .............. 715/525

FOREIGN PATENT DOCUMENTS

JP    2007179492 A  *  7/2007

OTHER PUBLICATIONS

Steven Holzner, Real World XML, Jan. 15, 2003, Peachpit Press.*
Rodolfo M. Raya, XML in localisation: Use XLIFF to translate documents, Oct. 2004, IBM DeveloperWorks.*

* cited by examiner

*Primary Examiner*—Stephen S Hong
*Assistant Examiner*—I-Chan Yang
(74) *Attorney, Agent, or Firm*—Townsend and Townsend and Crew LLP

(57) ABSTRACT

This disclosure describes systems, methods and software programs for transforming and/or translating a variety of documents, including without limitation XSL documents. In one aspect, any static information may be removed from XSL/FO files before transforming those files. This can greatly enhance the speed of transformation of such files. In another aspect, an XSL/FO file can be tagged in order to allow for the identification of the translatable data, such that the translatable data can be removed from the XSL/FO file and inserted into an XLIFF file. The translatable data can be then translated (e.g., by an automated process, by a human translator, etc.) and/or inserted back into an XSL file after translation.

16 Claims, 4 Drawing Sheets

METHODS AND SYSTEMS FOR EXTRACTING AND PROCESSING TRANSLATABLE AND TRANSFORMABLE DATA FROM XSL FILES

CROSS-REFERENCES TO RELATED APPLICATIONS

This application is a nonprovisional application claiming the benefit of provisional U.S. Patent Application No. 60/778,221, filed Mar. 1, 2006 by Xin Jiang et al. and entitled "XSL Transformation and Translation," the entire disclosure of which is incorporated herein by reference for all purposes.

FIELD OF THE INVENTION

The present invention relates in general to methods and systems of processing files and in particular to method and systems for transforming and translating documents organized according to a structured format.

BACKGROUND OF THE INVENTION

As increasingly more information becomes available online, automated tools for publishing information in a variety of formats, including without limitation standardized formats, become increasing important. One such tool commonly used is the eXtensible Markup Language ("XML"), a standard established by the World Wide Web Consortium ("W3C") for imposing structure on information. One skilled in the art will appreciate that XML is commonly used as a vehicle to distribute and/or maintain information in a structured format so that it can be used by disparate processes and tools. The XML standard also allows for relatively easy manipulation of data such that the data can be converted relatively easily into different formats for different purposes.

Oftentimes, a plurality of documents need to be formatted using a common format. In such situations, the eXtensible Stylesheet Language ("XSL"), another standard adopted by the W3C, can be used to provide a formatting template for a variety of documents which contain XML data. An extension to the XSL standard is the use of formatting objects ("FO"), which can provide formatting conventions for use within an XSL template for document. While Hypertext Markup Language ("HTML") provides layout information for information presented on the web, XSL and FO (collectively known as "XSL/FO") together provide a robust set of tools for page layout in more static forms (such as Portable Document Format ("PDF") files, printed pages, and the like).

The XSL standard also supports eXtensible Stylesheet Language Transformations ("XSLT"), which provide a hierarchical (tree-oriented) language for transforming instances of XML data into other forms. Merely by way of example, XSLT statements can be used to convert XML to HTML for screen display. Similarly, XSLT can be used to convert XML data to text in other formats such as portable document format ("PDF") and other XML documents with different schema.

Combining these two related technologies, an XSL/FO file commonly will have XSLT statements surrounded by XSL/FO statements which specify paragraph properties, font properties, color properties, layout properties, (such as tables, nested tables, columns, page sequences, etc.) and/or the like. In this way, the XSL/FO file can provide a robust template to provide formatting structure for various XML information. Hence, an XML transformation engine will apply XML data to the XSL/FO file (often using repeating and/or conditional formatting, perhaps based on the XSLT statements). In this way, the static formatting structure of the XSL/FO can be applied to dynamic XML data (such that a single XSL/FO file can be used to generate a plurality of formatted XML documents, using a plurality of XML datasets).

Generally, this transformation is performed in single step for each XML dataset. For example, an XSL transformation engine can be used to transform an XSL/FO file to an FO-XML file directly. However, since most of the data in a XSL/FO file is formatting data, which generally is static (i.e., does not change based on XML data applied) the transformation is relatively slow because the XSL transformation engine must process all of the static XSL/FO statements along with the dynamic XML data.

In addition, XML documents commonly need to be translated from one language to another. The XML localization interchange file format ("XLIFF") has been developed to facilitate the translation of XML documents in this manner. The XLIFF file format is used to store localizable data apart from formatting statements, such that the localizable data can be translated and reapplied to the formatting statements of the XML document. In many cases however, it is difficult to tell on an automated basis which data in a particular XSL or XML file is localizable and which data is static (e.g., formatting statements as described above). Hence, while the XLIFF format can facilitate the translation of documents there is no easy way to create the XLIFF file from an XSL/FO file.

Hence, it would be advantageous to provide a tool that could streamline the XSL transformation process. It would be further advantageous if such a tool could automate the process of creating XLIFF files to facilitate the subsequent translation of XSL documents from one language to another language.

BRIEF SUMMARY OF THE INVENTION

Embodiments of the invention provide novel systems, methods and software programs for transforming and/or translating a variety of documents, including without limitation XSL documents. In one aspect of some embodiments, any static information can be removed from XSL/FO files before transforming those files. This can greatly enhance the speed of transformation of such files. In an aspect of other embodiments of the invention, an XSL/FO file can be tagged in order to allow for the identification of the translatable data, such that the translatable data can be removed from the XSL/FO file and inserted into an XLIFF file. The translatable data can be then translated (e.g., by an automated process, by a human translator, etc.) and/or inserted back into an XSL file after translation. In some cases, both of these features can be combined, providing for rapid translation and transformation of an XSL file into an XML file or any other type of output file. Merely by way of example, the process can be used to create PDF files or Microsoft Word™ and Microsoft Excel™ documents, rich text format (RTF) files and/or the like.

One set of embodiments provide systems, including without limitations, systems for processing documents. An exemplary system might comprise a processor and a computer readable medium which might be in communication with the processor. The computer readable medium might comprise as a set of instructions, which may be executable by the processor. In a set of embodiments, the set of instructions includes instructions to analyze an XSL file comprising a set of data formatted according to a set of formatting objects to identify one or more elements of translatable data, and/or instructions to extract the elements of translatable data to produce an XLIFF file comprising these elements of translatable data. There may also be instructions to provide for the translation of the XLIFF file from a first language into a second language, thereby producing a set of translated data, which might comprising translations of at least some of the elements of translatable data. The set of translated data might then be merged into the XSL file to produce a translated XSL file.

In some embodiments, there may be instructions to analyze the data in the XSL file (which might be a translated XSL file, as indicated above), to identify a first portion of the data as static data, and/or to identify a second portion of the data as dynamic data. In some embodiments, further instructions may be executable to extract the static data from the XSL file, merely by way of example, to produce a modified XSL file comprising the dynamic data, and/or a static data file comprising the static data. Extracting the static data from the XSL file might comprise replacing each static data element with a corresponding token. The token, in some cases, might comprise less data than the static data element itself. In some cases, further instructions may provide for the translation of the static data in the static data file from a first language to a second language thereby producing a translated exact data file.

Optionally, there might be instructions to apply XML data to the modified XSL file, thereby creating intermediate file, which comprises the at least some of the XML data formatted according to a format specified by the XSL file. The intermediate file may be merged with the translated static data file to produce an output file, which can be formatted as specified by the XSL file and which can comprise XML data and/or the (possibly translated) static data of the XSL file. Merging the intermediate file with the translated the static data file might comprise replacing each token in the intermediate file with a corresponding static data element from the static data file. Various output file formats can be supported. Merely, by way of example, an output file may be an HTML file, an RTF file, a PDF file, Microsoft Word™ formatted file, a Microsoft Excel™ formatted file and/or the like.

Another set of embodiments provides methods, including without limitations methods of processing documents. An exemplary method might comprise analyzing (e.g., with a computer), an XSL file comprising a set of data. The first portion of this data may be static data and the second portion of the data may be dynamic data. The method might further comprise extracting the static data from the XSL file to produce a modified XSL file comprising the dynamic data and/or applying a set of XML data to the modified XSL file so as to create an intermediate file, which might comprise at least some of the XML data and/or might be formatted according to the formatting statements in the XSL file. The intermediate file may be merged with the static data extracted from the XSL file to produce an output file formatted according to the format of the XSL file; this output file might comprise at least some of the XML data and/or the static data of the XSL file.

In some cases, the XSL file may comprise a format defined at least in part by a set of formatting objects. In another set of embodiments, the static data may be stored in an XLIFF file. In such cases, the method might further comprise translating the static data in a modified XSL file from a first language into a second language. In further embodiments, the dynamic data may comprise one or more XSLT statements that operate on at least a portion of the XML data to generated format output.

In some cases, the static data may be extracted from the XSL file by replacing each static data element with a corresponding token which may comprise less data than the static data element itself. Applying a set of XML data to the modified XSL file, then, might comprise maintaining the tokens in the intermediate file; similarly, merging the intermediate file with the static data might comprise replacing each token in the intermediate file with a static data element corresponding to the token.

Another exemplary method might comprise analyzing an XSL file comprising a set of data formatted according to a set of formatting objects, to identify one or more elements of translatable data. The method, in some cases, further comprises extracting the one or more elements of translatable data to produce an XLIFF file comprising the elements of translatable data. The method can include providing for the translation of the XLIFF file from a first language to a second language, thereby producing a set of translated data comprising translations of at least some of the elements of translatable data. (In some cases, providing for the translation of the XLIFF file comprises providing the XLIFF file to a human translator for translation. In other cases, it might comprise a computer translating at least some of the elements of translatable data from the first language to the second language.) The method might further comprise merging the set of translated data into the XSL file to produce a translated XSL file.

In a particular embodiment, the method further comprises analyzing the translated XSL file to identify a first portion of the set of data as static data and to identify a second portion of the set of data as dynamic data. The static data may be extracted from the translated XSL file to produce a modified file comprising the dynamic data. The method might further comprise applying a set of XML data to the modified XSL file to create an intermediate file, which might comprise at least some of the XML data formatted according to a format specified by the translated XSL file. This intermediate file might be merged with the translated static data file to produce an output file, which might be an output file formatted as specified by the translated XSL file and/or might comprise at least some of the XML data and the static data of the translated XSL file.

Another set of embodiments provides computer programs, including without limitation computer programs that are executable by one or more computers to perform methods of the invention and/or computer programs that can be installed and/or executed on systems of the invention. An exemplary computer program, which might be embodied on a computer readable medium, might comprise a set of instructions. The set of instructions might include, without limitation, instructions to analyze an XSL file comprising a set of data, instructions to extract a set of static data from the XSL file to produce a modified XSL file comprising a set of dynamic data and/or a static data file comprising a set of static data. There may also be instructions to translate the static data in a static data file from a first language into a second language and/or instructions to merge the modified XSL file with the translated static data file to produce a translated XSL file.

BRIEF DESCRIPTION OF THE DRAWINGS

A further understanding of the nature and advantages of the present invention may be realized by reference to the remaining portions of the specification and the drawings, wherein like reference numerals are used throughout the several drawings to refer to similar components. In some instances, a sublabel is associated with a reference numeral to denote one of multiple similar components. When reference is made to a reference numeral without specification to an existing sublabel, it is intended to refer to all such multiple similar components.

DETAILED DESCRIPTION OF THE INVENTION

Figure 1:
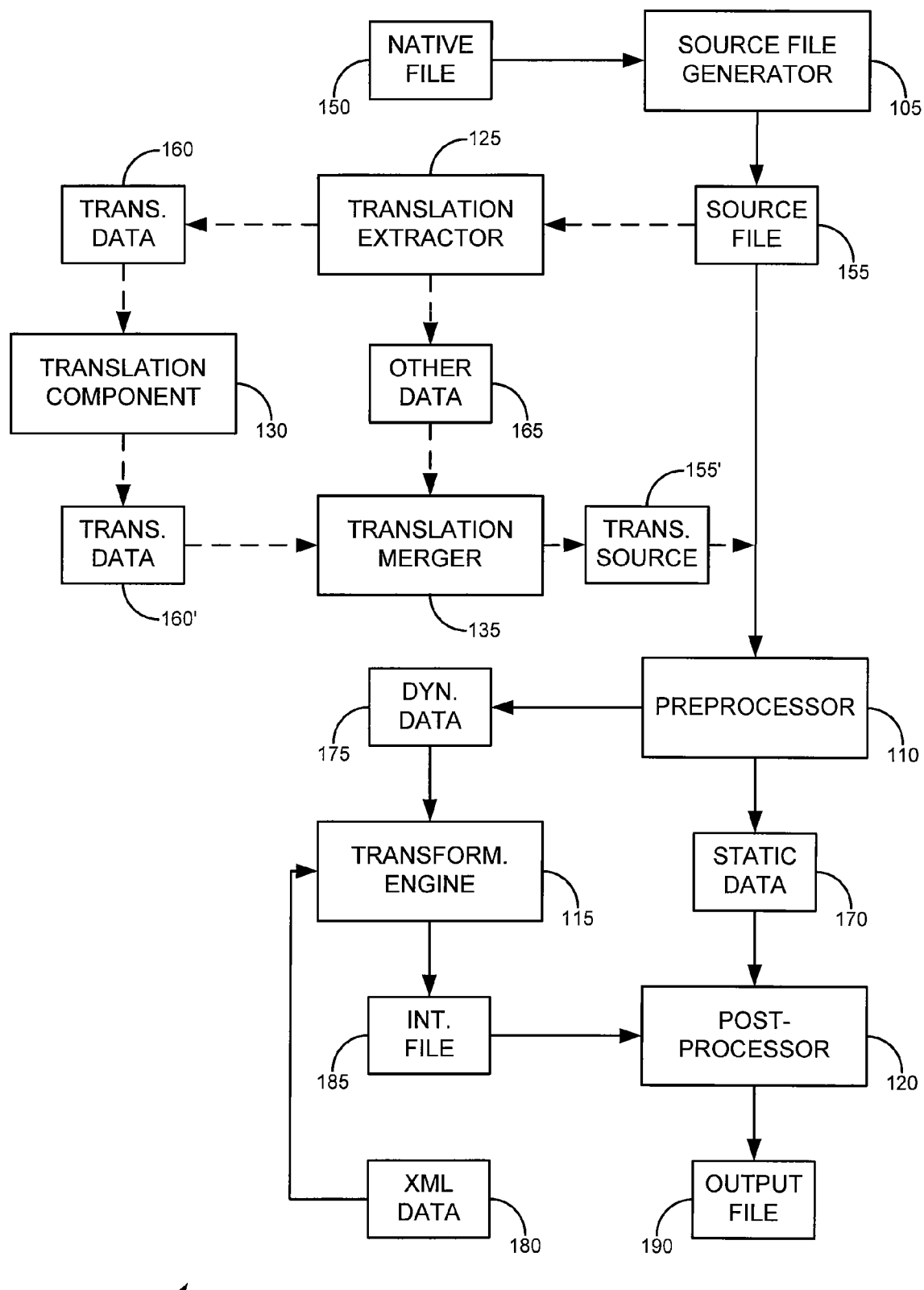
FIG. 1 is a functional diagram illustrating a system for transforming and/or translating document, in accordance with various embodiments of the invention.

Embodiments of the invention provide novel systems, methods and software programs for transforming and/or translating a variety of documents, including without limitation XSL files. One skilled in the art will appreciate that XSL files are often used to provide a formatting "template" that can be applied to one or more sets of XML data, allowing those XML data sets to be formatted and/or output in a consistent format. Hence, an XSL file, and in particular an XSL/FO file, often will contain both dynamic data and static data. As used herein, the term "dynamic data" is used to describe data (and in particular, data in an XSL or XSL/FO file) that is variable according to the XML data to which the XSL file is applied. Examples of dynamic data include references, conditional formatting statements, variables and/or the like, the values of which depend on the XML data used in transforming the XSL file. Conversely, the term "static data" is used to described data that remains consistent irrespective of the XML data to which the XSL file is applied. Examples of static data include "boilerplate" language, unconditional formatting statements and/or the like.

In the process of transforming an XSL/FO file, XML data is applied to the file, and the dynamic data is transformed according to the applied XML data, producing an FO-XML file as output (although, as noted below, other output formats ultimately can be provided as well). In an aspect of certain embodiments, this transformation process is implemented as a multi-step procedure, with a preprocessor removing static information (which would not be modified by the transformation) from the XSL/FO file before the transformation step. After transformation, the static information can be added back into the transformed file. This can greatly enhance the speed of transformation of such files.

In addition, when translating an XSL/FO file, certain data often will not need to be translated; for instance, certain dynamic data will not need to be translated in the XSL/FO file, at least in part because the XML data used to transform the dynamic data will already be translated; as another example, certain static data (such as formatting statements, etc.) will not need to be translated, because such data is language-independent. Hence, in an aspect of certain embodiments of the invention, an XSL/FO file can be tagged in order to allow for the identification of the translatable data, such that the translatable data can be removed from the XSL/FO file and inserted into an XLIFF file. The translatable data can be then translated (e.g., by an automated process, by a human translator, etc.) and/or inserted back into an XSL file after translation.

In some cases, both of these features can be combined, providing for rapid translation and transformation of an XSL file into an XML file or any other type of output file. Merely by way of example, the process can be used to create PDF files or Microsoft Word™ and Microsoft Excel™ documents, rich text format (RTF) files and/or the like.

FIG. 1 illustrates the functional components of a system 100 for transforming and/or translating files (including without limitation XSL/FO files) in accordance with certain embodiments of the invention. The structural arrangement of these functional components is discretionary; merely by way of example, each component could be implemented by a program (or sub-program within an application) running on a single computer. Alternatively and/or additionally, one or more computers may interoperate to provide the functional components of the system 100. It should be noted as well that, in some embodiments, one or more of the functional components illustrated by FIG. 1 and described herein may be omitted and/or modified, and/or additional functional components may be included.

(The operation of these functional components in accordance with an exemplary embodiment is described below with respect to the method 200 illustrated by FIG. 2. It should be noted, however, that the operation of the system 100 should not be understood to be limited to that method 200. Likewise, the method 200 of FIG. 2 can be performed by any suitable hardware and/or software, and therefore is not limited to the implementation illustrated by FIG. 1.)

The system 100 includes a source file generator 105, which can function to receive a file in a native format (such as a Microsoft Word document, etc.) and generate a source file (such as an XSL/FO file). The system 100 also includes a preprocessor 110, which prepares a file for transformation and/or translation; a transformation engine 115 which performs the XSL/FO transformation; and a postprocessor 120, which generates an output file from the transformed output of the preprocessor. In some cases, the system 100 may include a translation extractor 125 which identifies translatable data, and/or a translator 130, which provides for the translation of translatable data. There may also be a translation merger 135, which merges the translatable data back into the source file, to produce a translated source file.

Figure 2:
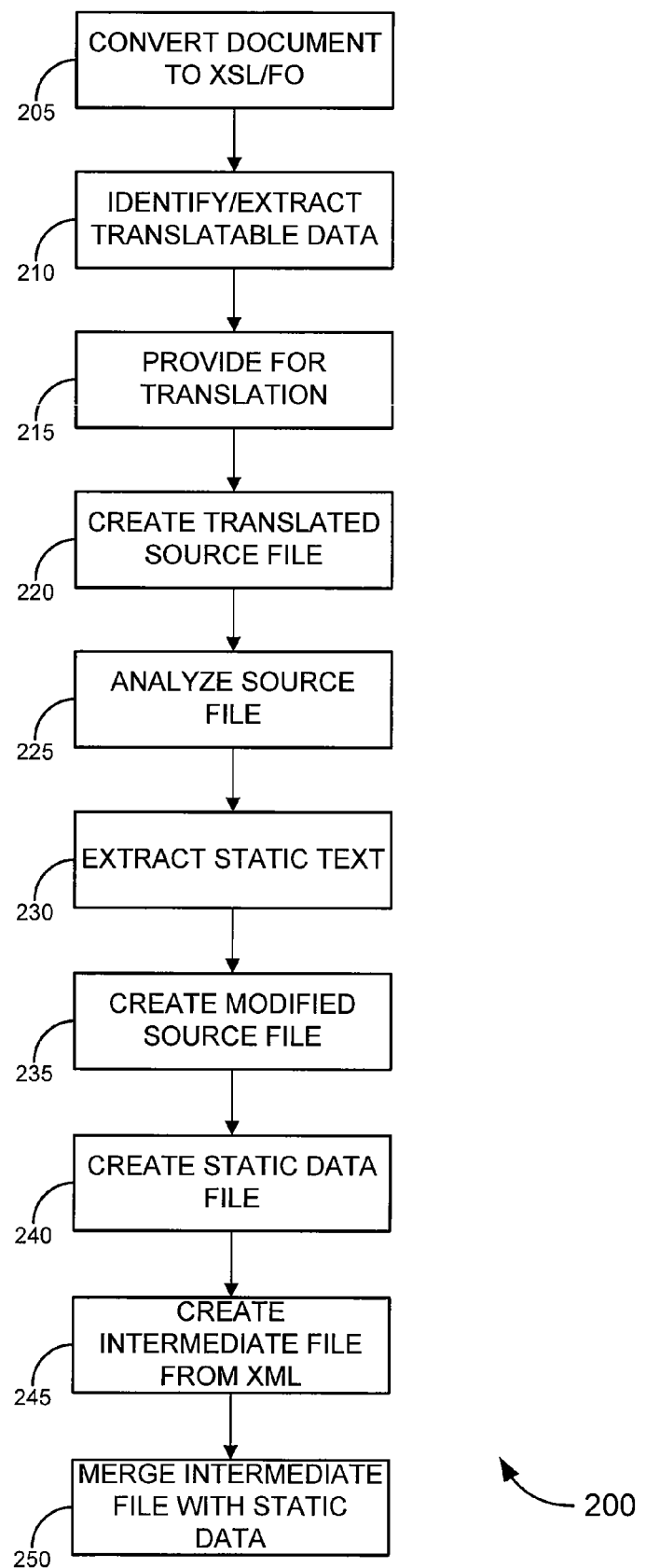
FIG. 2 is a process flow diagram illustrating a method of transforming and/or translating a document, in accordance with various embodiments of the invention.

In operation, the system 100 may perform the method 200 of FIG. 2 in accordance with some embodiments. (It should be appreciated that, while for ease of description, the method 200 is described with respect to the transformation and translation of a single source document, the method 200 also can be used in a batch mode to process multiple source files at once.) In accordance with some embodiments of the method 200, the source file generator 105 may receive one or more files 150 in a native format (such as a Word file, an Excel file, a PDF file, an XML file, an HTML file, etc.). The source file generator 105 processes the native file 150 by converting it to produce a source file 155, which in some cases is an XSL/FO stylesheet (block 205).

It should be noted that this procedure can be performed by a tool integrated with the transformation and/or translation tools and/or can be performed by a third party tool. Merely by way of example, one skilled in the art will appreciate, based on the disclosure herein, that there are many known tools for converting a native file to an XSL/FO stylesheet, and any of such tools may be used. Hence, the details of the conversion process need not be discussed extensively herein.

In certain embodiments, the source file 155 may be processed by a translation extractor 125, which identifies translatable data and/or extracts translatable data 160 from the source file 155 (block 210). In some cases, this procedure is performed before the source file is provided to the pre-processor 110. In a set of embodiments, the translation extractor 125 is configured to mark translatable portions of the source file 155. Translatable data can include, but is not limited to, static text in an XSL stylesheet. In most cases, there will be no need to translate dynamic XSL data (since the dynamic data will be replaced with specific XML data, as indicated below). Similarly, there generally will not be a need to translate formatting information in the source document (including FO and other structural information), since such data generally is language-independent (e.g., is designed to read by the transformation engine and/or an XML parser, not by human readers). Merely by way of example, in the element <fo:block>My name is: <xsl:value-of select="name"/></fo:block> the string My name is: would be translated. However, there would be no need to translate the tags (<fo:block> and </fo:block>) or the dynamic data (<xsl:value-of select="name"/>), because the former is language-independent, and the latter will be replaced with XML data during the transformation procedure (described below).

Thus, the translation extractor 125 may be configured to identify and/or extract those portions 160 of the source document that are translatable (i.e., amenable to translation). In some cases, extracting the portions of the source document that are translatable might comprise creating an XLIFF file comprising the translatable data 160. In a set of embodiments, the extraction of translatable data 160 might comprise replacing each instance of translatable data with a token in the source file 155, (as described below in more detail with respect to extraction of static data by the preprocessor, for example). The remaining, nontranslatable data 165 (perhaps comprising tokens replacing the translatable data) can be stored for later merging with translated data. In other embodiments, the translatable data might simply be marked in the source file 155, eliminating the need for extraction of the translatable data.

The translatable data 160 (and/or the entire source file, with translatable portions appropriately marked) then may be provided to a translation component 130 (block 215), which provides for the translation of the translatable data (e.g., from a first language, such as English, to one or more second languages, such as German, French, Spanish, etc.), to produce a translated source file 160. Providing for the translation of the translatable data 160 can take any of several forms. Merely by way of example, in some cases, the system 100 itself (and specifically the translation component 130) may perform automated translation. As noted above, in some cases, the translatable data 160 may be stored in an XLIFF file, known to those skilled in the art, to facilitate the translation process, and/or the translation component 130 may be configured to translate XLIFF files. Alternatively and/or in addition, the translation component 130 might interface with a separate tool configured to translate XLIFF files (Tools for automatically translating XLIFF files are available in the art, and specific discussion of such tools is outside the scope of this disclosure, except to note that any such suitable tool can be used.) In some cases, the system 100 might provide for the translation of translatable data 160 by providing that data to a human translator (and/or a separate translation tool). In some cases, both methods may be used: For example, an automated translation tool might make a first pass through the translatable data 160 to translate the data it can process, and the output of this tool might be provided to a human translator for error-checking and/or for translation of additional data that could not be processed by the automated tool.

At block 220, a translated source file is created. In accordance with embodiments that extract the translated data, the translation merger 135 may function to merge the translated data 160' with the other, non-translatable data (for example, by replacing each token in the source file with the translated data corresponding to that token), to produce a translated source file 155'. (In other embodiments, in which the translatable data is merely marked, but not extracted from the source file, the mere translation of the marked data can produce the translated source file 155').

The source file 155 (which may be a translated source file 155', if translation is performed, for example as described above) is then provided to the preprocessor 110, which analyzes the source file 155 (which, as indicated above, may be an XSL/FO stylesheet) to determine which portions of the source file 155 comprise static text and which portions comprise dynamic text (block 225). There are several procedures that can be used to perform such analysis. Merely by way of example, one skilled in the art will appreciate, based on the disclosure herein, that an XSL/FO stylesheet often will employ a Document Object Model ("DOM") tree, which provides a hierarchical structure for information in the stylesheet. A typical DOM tree for an element might take the following form:

```
<fo:block text-size="20" background-color="red">
    <xsl:value-of select="xmlelement"/>
</fo:block>
```

In this DOM tree, the element <xsl:value-of select="xmlelement"/> is dynamic data, while the remainder of the DOM tree comprises static data. In an embodiment of the invention, the preprocessor 110 thus may search the source file 155 for an appropriate term or namespace (such as "<xsl:"), which indicates the presence of dynamic data. This data may be marked as dynamic data, and other data in the stylesheet may be marked as static data. Other appropriate methods of distinguishing between dynamic and static data may be used as well. It should be noted that, in some cases, a dynamic element may be inextricably linked with a set of static data. In such cases, the static data may be treated as dynamic data by the preprocessor.

At block 230, the preprocessor 110 extracts the static data from the source document. In a set of embodiments, the extraction of static data may be performed by replacing an instance of static data with a token or placeholder. Merely by way of example, in the DOM tree above, the static data <fo:block text-size="20" background-color="red"> might be replaced with a token, such as, <__1>, which comprises substantially less data than the replaced static data, and which therefore is less expensive computationally during the transformation process. (In addition, the transformation process might be configured to ignore the tokens, if the tokens are named using an identifiable scheme, further expediting the transformation process.) The replaced static data can be stored in any suitable form, such as in a flat file, in a database, and/or the like. In a set of embodiments, a substitution table, comprising each token and its corresponding replaced text, can be used to track the replaced text.

Thus, in an embodiment, the preprocessing engine creates a static data file 170 (block 235), comprising the static data removed from the source file 155 (this static data file might include the substitution table and/or might rely on a separate substitution table), as well as a modified source file 175 comprising the dynamic data and the tokens (which replaced the static data) (block 240). Merely by way of example, if the source file is an XSL/FO stylesheet, the modified source file might comprise the dynamic data (such as XSL variables, references, etc) from that stylesheet, with tokens for static data, such as formatting information, static text, and/or the like. (Each of these files may be stored in a file system, database, etc. as appropriate, and/or might simply be stored in RAM.)

The modified source file 175 comprising the dynamic data is processed by the transformation engine 115, using one or more sets of provided XML data 180. An XSL/FO transformation process similar to XSL/FO transformations known to those skilled in the art may be used in some embodiments, except that the XSL/FO file has been modified, as described above, to remove static data. This can greatly decrease the computational expense (and therefore, generally enhance the speed) of the transformation process. In a set of embodiments, the processing by the transformation engine 115 creates (block 235) one or more intermediate files (for example an FO-XML file) 185, which might comprise data based on the supplied XML data 180, as well as formatting objects based on the modified XSL/FO file 170. Hence, in an embodiment, the intermediate file comprises at least some of the XML data, formatted according to a format specified by the XSL/FO file. Because, as noted above, some embodiments replace certain static data with tokens or other placeholders, the process of transforming the modified XSL/FO file might be configured to maintain these tokens in their original form in the intermediate file 180, so that the tokens can later be replaced by the substituted static data.

In some embodiments, the intermediate file(s) 185, along with the static data 170 are provided to a post-processor 120, which merges the static data with the output from the transformation engine (block 240) to produce an output file 185. As noted above, in some embodiments, the static data is replaced by one or more tokens by the pre-processor 110. Merging the intermediate file 185 with the static data 170, then, might comprise replacing the tokens with the corresponding static data (e.g., according to a set of relationships between tokens and corresponding static data, as recorded in a substitution table).

The output file 190 can take any of several forms. In some cases, the output file might be an FO-XML file. In other cases, the output file might be an HTML file, a Microsoft Word document, a Microsoft Excel document, an RTF document, a PDF document and/or any other suitable document format. In some embodiments, the postprocessor 120 might be configured to support output of these file types. In other embodiments, the postprocessor might be configured to output documents of a particular type (e.g., FO-XML documents), and an additional tool might be used to convert those documents into the appropriate output file type.

This disclosure generally, and in particular with respect to the method 200, above, describes "creating," "generating," "producing" and "converting" various documents and tiles. It should he noted that these terms are used interchangeably, unless the context clearly dictates otherwise. Merely by way of example, block 245 above describes creating an intermediate file. This creation of the intermediate file could merely comprise converting the modified source file into the intermediate file. (Alternatively, an entirely new file could be created.) At block 250, the intermediate file is merged with the static data. Likewise, while block 205 describes converting a native file into a source file, that conversion could comprise creating the source file as a new file, based on the native file.

Figure 3:
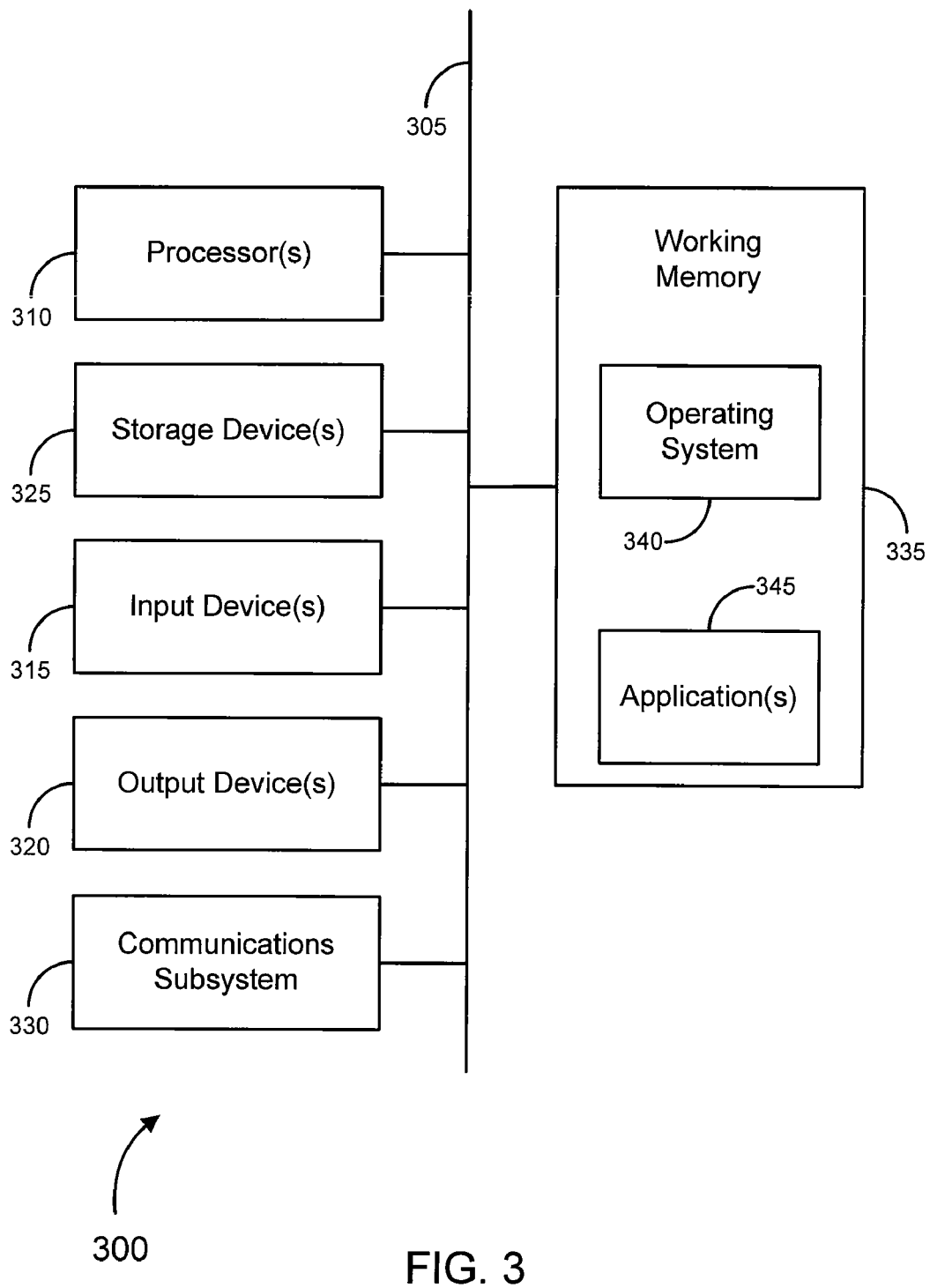
FIG. 3 is a generalized schematic diagram illustrating a computer that can be used to transform and/or translate documents, in accordance with various embodiments of the invention.

FIG. 3 provides a schematic illustration of one embodiment of a computer system 300 that can perform the methods of the invention and/or the functions of a document translation and/or transformation system, as described herein. It should be noted that FIG. 3 is meant only to provide a generalized illustration of various components, any or all of which may be utilized as appropriate. FIG. 3, therefore, broadly illustrates how individual system elements may be implemented in a relatively separated or relatively more integrated manner. The computer system 300 is shown comprising hardware elements that can electrically coupled via a bus 305 (or may otherwise be in communication, as appropriate). The hardware elements can include one or more processors 310, including without limitation one or more general-purpose processors and/or one or more special-purpose processors (such as digital signal processing chips, graphics acceleration chips, and/or the like); one or more input devices 315, which can include without limitation a mouse, a keyboard and/or the like; and one or more output devices 320, which can include without limitation a display device, a printer and/or the like.

The computer system 300 may further include (and/or be in communication with) one or more storage devices 325, which can comprise, without limitation, local and/or network accessible storage and/or can include, without limitation, a disk drive, a drive array, an optical storage device, solid-state storage device such as a random access memory ("RAM") and/or a read-only memory ("ROM"), which can be programmable, flash-updateable and/or the like. The computer system 3 might also include a communications subsystem 330; which can include without limitation a modem, a network card (wireless or wired), an infra-red communication device, and/or the like), a wireless communication device and/or chipset (such as a Bluetooth™ device, an 802.11 device, a WiFi device, a WiMax device, cellular communication facilities, etc.). The communications system 330 may permit data to be exchanged with a network and/or any other devices described herein. In many embodiments, the computer system 300 will further comprise a memory 335, which can include a RAM or ROM device, as described above.

The computer system 300 also can comprise software elements, shown as being currently located within a working memory 335, including an operating system 340 and/or other code 345, such as one or more application programs, which may comprise computer programs of the invention and/or may be designed to implement methods of the invention, as described herein. It will be apparent to those skilled in the art that substantial variations may be made in accordance with specific requirements. For example, customized hardware might also be used and/or particular elements might be implemented in hardware, software (including portable software, such as applets), or both. Further, connection to other computing devices such as network input/output devices may be employed.

Figure 4:
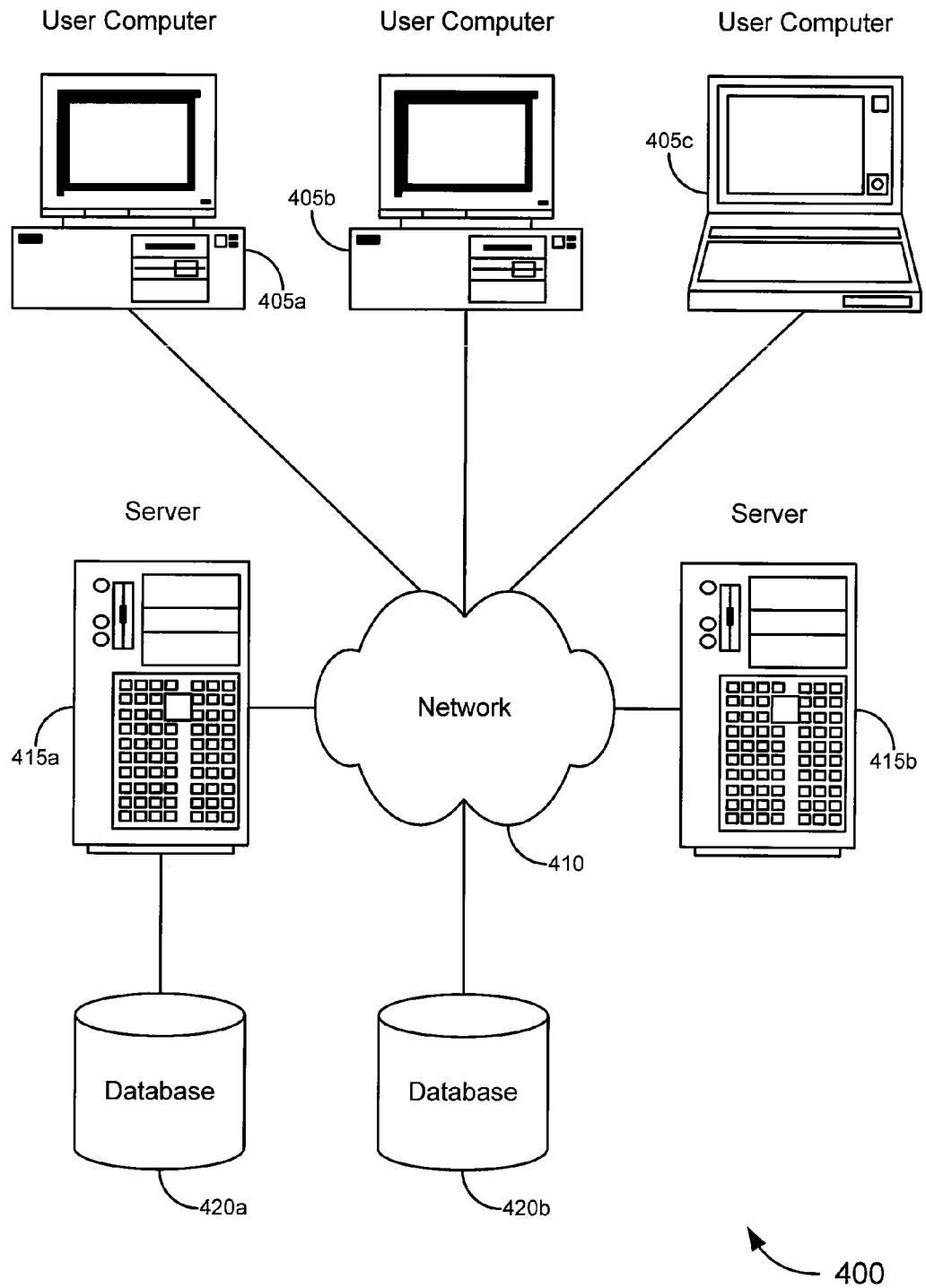
FIG. 4 is a block diagram illustrating a system of computers that can be used to transform and/or translate documents, in accordance with various embodiment of the invention.

Other systems might comprise more than one computer. Merely by way of example, the functional components described with respect to FIG. 1 above may be distributed among a plurality of computers. Hence, FIG. 4 illustrates a schematic diagram of a system 400 that can be used in accordance with one set of embodiments. The system 400 can include one or more user computers 405. A user computer may, for example, be used to perform one or more of the functions described with respect to FIGS. 1 and 2 and/or to provide data and/or commands to one or more server computers (such as those described below), which might perform such functions.

The user computers 405 can be general purpose personal computers (including, merely by way of example, personal computers and/or laptop computers running any appropriate flavor of Microsoft Corp.'s Windows™ and/or Apple Corp.'s Macintosh™ operating systems) and/or workstation computers running any of a variety of commercially-available UNIX™ or UNIX-like operating systems. These user computers 405 can also have any of a variety of applications, including one or more applications configured to perform methods of the invention, as well as one or more office applications, database client and/or server applications, and web browser applications. Alternatively, the user computers 405 can be any other electronic device, such as a thin-client computer, Internet-enabled mobile telephone, and/or personal digital assistant, capable of communicating via a network (e.g., the network 410 described below) and/or displaying and navigating web pages or other types of electronic documents. Although the exemplary system 400 is shown with three user computers, any number of user computers can be supported.

Certain embodiments of the invention operate in a networked environment, which can include a network 410. The network 410 can be any type of network familiar to those skilled in the art that can support data communications using any of a variety of commercially-available protocols, including without limitation TCP/IP, SNA, IPX, AppleTalk, and the like. Merely by way of example, the network 410 can be a local area network ("LAN"), including without limitation an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network, including without limitation a network operating under any of the IEEE 802.11 suite of protocols, the Bluetooth™ protocol known in the art, and/or any other wireless protocol; and/or any combination of these and/or other networks.

As noted above, some embodiments of the invention can include one or more server computers 415. Each of the server computers 415 may be configured with an operating system including without limitation any of those discussed above, as well as any commercially-available server operating systems. Each of the servers 415 may also be running one or more applications, which can be configured to perform the functionality of the invention and/or to provide services to one or more clients 405 and/or other servers 415.

Merely by way of example, one of the servers 415 may be a web server, which can be used, merely by way of example, to process requests for web pages or other electronic documents from user computers 405. As a specific example, a web server 415 can be configured to serve output documents to users. The web server can also run a variety of server applications, including HTTP servers, FTP servers, CGI servers, database servers, Java servers, and/or the like. In some embodiments of the invention, the web server may be configured to serve web pages and/or other documents (including without limitation output documents from a transformation/translation process), which can be viewed within a web browser on one or more of the user computers 405 to perform methods of the invention.

The server computers 415, in some embodiments, might include one or more file and or/application servers, which can include one or more applications accessible by a client running on one or more of the client computers 405 and/or other servers 415. Merely by way of example, the server(s) 415 can be one or more general purpose computers capable of executing programs or scripts in response to the user computers 405 and/or other servers 415, including without limitation web applications and/or services (which might, in some cases, be configured to perform methods of the invention).

Merely by way of example, a web application can be implemented as one or more scripts or programs written in any programming language, such as Java™, C, C#™ or C++, and/or any scripting language, such as Perl, Python, or TCL, as well as combinations of any programming/scripting languages. The application server(s) can also include database servers, including without limitation those commercially available from Oracle, Microsoft, Sybase™, IBM™ and the like, which can process requests from database clients running on a user computer 405 and/or another server 415.

In some embodiments, an application server can create web pages dynamically for displaying the information in accordance with embodiments of the invention, such as transformed and/or translated data. Data provided by an application server may be formatted as XML documents (including FO-XML documents, as described above), web pages (comprising HTML, Javascript, etc., for example) and/or may be forwarded to a user computer 405 via a web server (as described above, for example). Similarly, a web server might receive web page requests and/or input data from a user computer 405 and/or forward the web page requests and/or input data to an application server.

In accordance with further embodiments, one or more servers 415 can function as a file server and/or can include one or more of the files necessary to implement methods of the invention incorporated by an application running on a user computer 405 and/or another server 415. Alternatively, as those skilled in the art will appreciate, a file server can include all necessary files, allowing such an application to be invoked remotely by a user computer 405 and/or server 415. It should be noted that the functions described with respect to various servers herein (e.g., application server, database server, web server, file server, etc.) can be performed by a single server and/or a plurality of specialized servers, depending on implementation-specific needs and parameters.

In certain embodiments, the system 400 can include one or more data stores, including without limitation one or more databases 420. The data store can be used to store information (such as XML data, source files, output files, static and/or dynamic data files, etc.) used and/or generated by methods of the invention. The location of the data store(s) and/or database(s) 420 is discretionary: merely by way of example, a database 420a might reside on a storage medium local to (and/or resident in) a server 415a (and/or a user computer 405). Alternatively, a database 420b can be remote from any or all of the computers 405, 415, so long as it can be in communication (e.g., via the network 410) with one or more of these. In a particular set of embodiments, a database 420 can reside in a storage-area network ("SAN") familiar to those skilled in the art. (Likewise, any necessary files for performing the functions attributed to the computers 405, 415 can be stored locally on the respective computer and/or remotely, as appropriate.) In one set of embodiments, the database 435 can be a relational database, such as an Oracle database, that is adapted to store, update, and retrieve data in response to SQL-formatted commands. The database might be controlled and/or maintained by a database server, as described above, for example.

While the invention has been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods of the invention are not limited to any particular structural and/or functional architecture but instead can be implemented on any suitable hardware, firmware and/or or software configuration. Similarly, while various functionality is ascribed to certain system components, unless the context dictates otherwise, this functionality can be distributed among various other system components in accordance with different embodiments of the invention.

Moreover, while the procedures comprised in the methods and processes described herein are described in a particular order for ease of description, unless the context dictates otherwise, various procedures may be reordered, added, and/or omitted in accordance with various embodiments of the invention. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary features, the various components and/or features described herein with respect to a particular embodiment can be substituted, added and/or subtracted from among other described embodiments, unless the context dictates otherwise. Consequently, although the invention has been described with respect to exemplary embodiments, it will be appreciated that the invention is intended to cover all modifications and equivalents within the scope of the following claims.

What is claimed is:

1. A system for processing a document, the system comprising:
    a processor;
    a computer readable medium in communication with the processor and comprising a set of instructions executable by the processor, the set of instructions comprising:
        a) instructions to analyze an eXtended Stylesheet Language ("XSL") file comprising a set of data formatted according to a set of formatting objects ("FO"), to identify one or more elements of translatable data;
        b) instructions to extract the one or more elements of translatable data to produce an eXtended Markup Language Localization Interchange File Format ("XLIFF") file comprising the one or more elements of translatable data;
        c) instructions to provide for the translation of the XLIFF file from a first language to a second language to produce a set of translated data comprising translations of at least some of the one or more elements of translatable data;
        d) instructions to merge the set of translated data into the XSL file to produce a translated XSL file;
        e) instructions to analyze the data in the translated XSL file to identify a first portion of the data as static data and to identify a second portion of the data as dynamic data;
        f) instructions to extract the static data from the translated XSL file to produce a modified XSL file comprising the dynamic data, wherein extracting the static data from the XSL file comprises replacing each static data element with a corresponding token, the token comprising less data than the static data element;
        g) instructions to apply a set of eXtended Markup Language ("XML") data to the modified XSL file to create an intermediate file comprising at least some of the XML data formatted according to a format specified by the XSL file; and
        h) instructions to merge the intermediate file with the static data to produce an output file formatted as specified by the XSL file and comprising at least some of the XML data and the static data of the XSL file, wherein merging the intermediate file with the static data comprises replacing each token in the intermediate file with a corresponding static data element from the static data.

2. A system as recited by claim 1, wherein the output file is selected from the group consisting of a HyperText Markup Language ("HTML") file, a Rich Text Format ("RTF") file, a Portable Document File ("PDF"), a Microsoft Word-formatted file, and a Microsoft Excel-formatted file.

3. A system as recited by claim 1, wherein providing for the translation of the XLIFF file comprises providing the XLIFF file to a human translator for translation.

4. A system as recited by claim 1, wherein providing for the translation of the XLIFF file comprises a computer translating at least some of the one or more elements of translatable data from the first language to the second language.

5. A method of processing a document, the method comprising:
    analyzing, with a computer, an eXtended Stylesheet Language ("XSL") file comprising a set of data, wherein a first portion of the data is static data and wherein a second portion of the data is dynamic data;
    extracting the static data from the XSL file to produce a modified XSL file comprising the dynamic data;
    applying a set of eXtended Markup Language ("XML") data to the modified XSL file to create an intermediate file comprising at least some of the XML data formatted according to a format specified by the XSL file; and
    merging the intermediate file with the static data extracted from the XSL file to produce an output file formatted as specified by the XSL file and comprising at least some of the XML data and the static data of the XSL file.

6. A method as recited by claim 5, wherein the XSL file comprises a format defined at least in part by a set of formatting objects ("FO").

7. A method as recited by claim 5, further comprising:
    analyzing the XSL file to identify one or more elements of translatable data;
    extracting the one or more elements of translatable data to produce an eXtended Markup Language Localization Interchange File Format ("XLIFF") file comprising the one or more elements of translatable data;
    providing for the translation of the XLIFF file from a first language to a second language to produce a set of translated data comprising translations of the one or more elements of translatable data; and
    merging the set of translated data into the XSL file.

8. A method as recited by claim 5, wherein the dynamic data comprises one or more eXtensible Stylesheet Language Transformation ("XSLT") statements that operate on at least a portion of the XML data to generate formatted output.

9. A method as recited by claim 5, wherein:
    extracting the static data from the XSL file comprises replacing each static data element with a corresponding token, wherein the token comprises less data than the static data element;
    applying the set of XML data to the modified XSL file comprises maintaining the tokens in the intermediate file; and
    merging the intermediate file with the static data comprises replacing each token in the intermediate file with a static data element corresponding to the token.

10. A method as recited by claim 5, wherein the dynamic data comprises a static XSL element with a dynamic attribute, such that the static XSL element is treated as dynamic data.

11. A method as recited by claim 5, further comprising:
    creating the XSL file by converting a document from a native format into an XSL/FO document.

12. A system for processing a document, the system comprising:

means for analyzing an eXtended Stylesheet Language ("XSL") file comprising a set of data, wherein a first portion of the data is static data and wherein a second portion of the data is dynamic data;

means for extracting the static data from the XSL file to produce a modified XSL file comprising the dynamic data;

means for applying a set of eXtended Markup Language ("XML") data to the modified XSL file to create an intermediate file comprising at least some of the XML data formatted according to a format specified by the XSL file; and means for merging the intermediate file with the static data extracted from the XSL file to produce an output file formatted as specified by the XSL file and comprising at least some of the XML data and the static data of the XSL file.

13. A method of processing a document, the method comprising:

analyzing, by a preprocessor system, an eXtended Stylesheet Language ("XSL") file comprising a set of data formatted according to a set of formatting objects ("FO"), to identify one or more elements of translatable data;

extracting, by a translation extractor system, the one or more elements of translatable data to produce an eXtended Markup Language Localization Interchange File Format ("XLIFF") file comprising the one or more elements of translatable data;

providing, by the translation extractor system, for the translation of the XLIFF file from a first language to a second language to produce a set of translated data comprising translations at least some of the one or more elements of translatable data;

merging, by a translation merger system, the set of translated data into the XSL file to produce a translated XSL file;

analyzing the translated XSL file to identify a first portion of the set of data as static data and to identify a second portion of the set of data as dynamic data;

extracting static data from the translated XSL file to produce a modified XSL file comprising the dynamic data;

applying a set of eXtended Markup Language ("XML") data to the modified XSL file to create an intermediate file comprising at least some of the XML data formatted according to a format specified by the translated XSL file; and merging the intermediate file with the static data extracted from the translated XSL file to produce an output file formatted as specified by the translated XSL file and comprising at least some of the XML data and the static data of the translated XSL file.

14. A method as recited by claim 13, wherein providing for the translation of the XLIFF file comprises providing the XLIFF file to a human translator for translation.

15. A method as recited by claim 13, wherein providing for the translation of the XLIFF file comprises a computer translating at least some of the one or more elements of translatable data from the first language to the second language.

16. A method as recited by claim 13, wherein:

extracting the static data from the translated XSL file comprises replacing each static data element with a corresponding token, wherein the token comprises less data than the static data element;

applying the set of XML data to the modified XSL file comprises maintaining the tokens in the intermediate file; and merging the intermediate file with the translated static data file comprises replacing each token in the intermediate file with a translated static data element corresponding to the token.

* * * * *